(12) United States Patent
Requardt et al.

(10) Patent No.: US 10,363,009 B2
(45) Date of Patent: Jul. 30, 2019

(54) METHOD AND APPARATUS FOR CORRECTION OF A SYNTHETIC ELECTRON DENSITY MAP

(71) Applicants: Martin Requardt, Nürnberg (DE); Nora Hünemohr, Stuttgart (DE)

(72) Inventors: Martin Requardt, Nürnberg (DE); Nora Hünemohr, Stuttgart (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/713,068

(22) Filed: Sep. 22, 2017

(65) Prior Publication Data

US 2018/0085080 A1 Mar. 29, 2018

(30) Foreign Application Priority Data

Sep. 23, 2016 (DE) .......................... 10 2016 218 359

(51) Int. Cl.
*A61B 6/00* (2006.01)
*A61B 6/03* (2006.01)
(Continued)

(52) U.S. Cl.
CPC ............ *A61B 6/5229* (2013.01); *A61B 5/055* (2013.01); *A61B 6/037* (2013.01); *A61N 5/1039* (2013.01); *G01R 33/4812* (2013.01); *G06N 20/00* (2019.01); *G06T 7/0012* (2013.01); *G06T 2207/10081* (2013.01);
(Continued)

(58) Field of Classification Search
USPC .......................................................... 600/410
See application file for complete search history.

(56) References Cited

U.S. PATENT DOCUMENTS

| 2009/0135202 A1 | 5/2009 | Keuenhof |
| 2011/0007959 A1* | 1/2011 | Schulz .................. A61B 5/055 382/131 |

(Continued)

FOREIGN PATENT DOCUMENTS

| CN | 101441863 A | 5/2009 |
| CN | 105659104 A | 6/2016 |

(Continued)

OTHER PUBLICATIONS

Dixon, Thomas W., "Simple Proton Spectroscopic Imaging", Radiology, 1984, vol. 153, pp. 184-194.
(Continued)

*Primary Examiner* — Carolyn A Pehlke
*Assistant Examiner* — Marjan Saboktakin
(74) *Attorney, Agent, or Firm* — Sempia Summerfield Katz LLC

(57) ABSTRACT

Systems and methods are provided for determining a synthetic electron density map based on at least one MR image dataset and based on at least one soft tissue image structure and one bone image structure determined in the synthetic electron density map. The soft tissue image structure and the bone image structure may be compared with the corresponding structures in the MR image dataset. From a correction of the first soft tissue image structure and/or of the bone image structure is based on the comparison, a corrected synthetic electron density map is determined.

17 Claims, 4 Drawing Sheets

(51) Int. Cl.
*A61N 5/10* (2006.01)
*G06T 7/00* (2017.01)
*A61B 5/055* (2006.01)
*G01R 33/48* (2006.01)
*G06N 20/00* (2019.01)

(52) U.S. Cl.
CPC .............. *G06T 2207/10088* (2013.01); *G06T 2207/30008* (2013.01); *G06T 2207/30024* (2013.01)

(56) References Cited

U.S. PATENT DOCUMENTS

| | | |
|---|---|---|
| 2015/0238148 A1 | 8/2015 | Georgescu et al. |
| 2016/0238684 A1 | 8/2016 | Steinbach et al. |

FOREIGN PATENT DOCUMENTS

| | | | |
|---|---|---|---|
| WO | WO2015059616 A1 | 4/2015 | |
| WO | WO2015150065 A1 | 10/2015 | |
| WO | WO 2015171056 A1 * | 11/2015 | ........... A61N 5/1039 |
| WO | WO2015171056 A1 | 11/2015 | |
| WO | WO 2016166071 * | 10/2016 | ............... A61N 5/10 |

OTHER PUBLICATIONS

Dowling, Jason A. et al.: "Automatic Substitute Computed Tomography Generation and Contouring for Magnetic Resonance Imaging (MRI)-Alone External Beam Radiation Therapy From Standard MRI Sequences", in: Int J Radiation Oncol Biol Phys, vol. 93, No. 5, pp. 1144-1153, 2015.

German Office Action for related German Application No. 10 2016 218 359.1 dated May 29, 2017.

Hsu, Shu-Hui et al; "Investigation of a method for generating synthetic CT models from MRI scans of the head and neck for radiation therapy"; in: Phys Med Biol.; vol. 58; No. 23; Dec. 7, 2013.

Chinese Office Action for Chinese Application No. 201710858354.3 dated Oct. 8, 2018 with English Translation.

* cited by examiner

METHOD AND APPARATUS FOR CORRECTION OF A SYNTHETIC ELECTRON DENSITY MAP

CROSS REFERENCE TO RELATED APPLICATIONS

This application claims the benefit of DE 102016218359.1 filed on Sep. 23, 2016 which is hereby incorporated by reference in its entirety

FIELD

Embodiments relate to medical imaging techniques.

BACKGROUND

In radiation therapy (radiotherapy) a part of the tissue of a patient is irradiated with ionizing radiation in order to change the tissue part or a surrounding area including the tissue part. An external radiotherapy is known that includes an irradiation of the body of the patient from outside the body. Also known is an internal radiotherapy by radiation sources that include radioactive substances. The radiation sources are introduced into the body of the patient in order to damage or to destroy the tissue part locally in the body of the patient.

A radiotherapy may be planned and/or monitored by medical imaging methods. A radiotherapy plan based on a medical imaging dataset of the patient is created. Computed tomography image datasets (CT image datasets) are used. On the basis of the CT image datasets, the target volume of the radiotherapy may be defined and a surrounding tissue sensitive to radiation may be localized. The intensity values of the image voxels of the image data (measured in Hounsfield Units) are a good approximation for mapping an electron density at the corresponding location in the body of the patient, since the intensity value of an image voxel is based on an absorption of the x-ray radiation at the associated location. The CT image datasets may be converted for the radiotherapy planning into an electron density map. Since in radiotherapy the cross-section of the interaction of the radiation correlates in a positive way with the electron density in the body, the attenuation of the radiation during its passage through the body may be computed from the CT image datasets.

Other imaging methods with a better soft tissue contrast may be used in radiotherapy planning in order to make possible an improved identification of target organs and/or organs at risk. One such method is the recording of magnetic resonance image datasets (abbreviated to MR image dataset) using a magnetic resonance device. Since image contrasts of the MR image dataset do not have any physical relationship to electron density, no direct conclusions may be drawn therefrom about the electron density and thus the photon attenuation in the patient. For example, both bone and also air regions do not show any signal in MR contrasts and are displayed dark in an MR image dataset, although the regions have a different electron density and thus a different photon attenuation. For planning of a radiotherapy, in addition to the MR image dataset, a CT dataset is determined, that provides electron densities with the necessary precision for the radiotherapy. However, different positions of the patient and changes in the anatomy of the patient may be taken into account between the two examinations (e.g. changes in volume from air breathed in). The corresponding resources, e.g. CT devices and trained operating personnel, may be retained and available.

MR image datasets may be used for radiotherapy planning and for dispensing with the recording of additional CT image datasets (exclusively magnetic resonance-based radiotherapy planning, "MR Only Radiotherapy Planning", abbreviated to MRORTP), and may be used to define synthetic electron density maps without the use of CT image datasets of the examined patient. A synthetic electron density map needed for radiotherapy planning and dose calculation is only been able to be determined from the MR image dataset with high algorithmic outlay and with susceptibility to errors.

Publication WO 2015/171056 A1 discloses that a synthetic electron density map may be determined on the basis of an MR image dataset. The MR image dataset is initially segmented and an electron density map already known beforehand is converted into a synthetic electron density map by applying a transformation (e.g. a registration) based on the segmented MR image dataset.

SUMMARY AND DESCRIPTION

The scope of the present invention is defined solely by the appended claims and is not affected to any degree by the statements within this summary. The present embodiments may obviate one or more of the drawbacks or limitations in the related art.

Embodiments provide a method for determining a corrected synthetic electron density map. The method includes determining a first synthetic electron density map of the patient based on at least one MR image dataset and determining of at least one first soft tissue image structure and/or at least of one first bone image structure based on of the first synthetic electron density map. The method includes a comparison of the first soft tissue image structure and/or of the first bone image structure from the first synthetic electron density map with corresponding image structures in the MR image dataset. Errors in the determination of the first synthetic electron density map may be identified by the comparison, since a stronger contrast between bone image structures and soft tissue image structures is present both in a synthetic electron density map and also in the MR image dataset. The MR image dataset may serve as a reference for the synthetic electron density map. The method includes the determination of a corrected synthetic electron density map through correction of the first soft tissue image structure and/or of the first bone image structure based on the comparison. For radiotherapy planning, differentiation between bone image structures and soft tissue image structures may be sufficient, since the differences of the electron density within a bone region or within a soft tissue region of the patient are negligible for the radiotherapy. For the determination of the radiation dose taken up in a body a determination is made of whether the body volume belongs to a soft tissue region or to a bone region. Through a correction of the first soft tissue image structure and/or of the bone image structure based on the comparison, a corrected synthetic electron density map may be determined.

In an embodiment, the first synthetic electron density map is determined by a magnetic resonance tomography-computed tomography atlas (MR-CT atlas). An MR-CT atlas refers to a collection of MR image datasets, of associated CT image datasets of the same body regions of the same patients, as well as optionally of associated registrations. The determination of a first synthetic electron density map by an MR-CT atlas includes the advantage that no additional imaging with the MR device (e.g. with specific sequences) is necessary, and that thus the examination time of the patient may be reduced. Variations in the electron density of a bone region of the patient able to be resolved by CT imaging may be taken into account in the determination of the first synthetic electron density.

In an embodiment, the comparison of the first soft tissue image structure and/or of the first bone image structure is made by a result image that is determined by the combination of the first soft tissue image structure and/or of the first bone image structure with the MR image. A result image exhibits a high information density and allows differences between the first soft tissue image structure and/or the first bone image structures of the first synthetic electron density map and the corresponding structures of the MR image dataset to be recognized. Automatic and fully automatic methods for image recognition and processing are known that may be used on the basis of a result image for the comparison. The result image may be a three-dimensional representation or also a two-dimensional representation. A two-dimensional representation may for example be created by a section through a three-dimensional image dataset. A result image may also be a representation of a number of images alongside one another and/or above one another.

In an embodiment, the result image includes the MR image dataset. At least a part of the first soft tissue image structure and/or at least a part of the first bone image structure is shown in the MR image dataset. A representation directly in the MR image dataset includes the advantage that the comparison may be made based only on the MR image dataset or only on an image from the MR image dataset. The resulting higher information density makes possible a faster and more precise comparison by an operator. The representation may be undertaken so that pixels or voxels belonging to the first soft tissue image structure and/or to the first bone image structure are marked in the MR image. A marking may be with a single color value that differs from the color values already used in the representation of the MR dataset. The marking may be a color palette, by the pixel color or voxel color of a soft tissue image structure or bone image structure determined from the color palette in accordance with the pixel value or voxel value in the synthetic electron density. For example, all color values of the color palette may differ from the color values already used in the representation of the MR image dataset.

In an embodiment, at least the edge of the image structure in the MR image dataset is shown as part of the first soft tissue image structure and/or of the first bone image structure. Since the edge of an image structure may be shown without any covering of pixels or voxels in the result image, such a representation includes the advantage that, in the result image, as well as the first image structures, at the same time the complete contrast information of the MR image dataset in all pixels or voxels may be shown. The edge of a two-dimensional image structure is the one-dimensional line delimiting the image structure, the edge of a three-dimensional image structure is the two-dimensional surface delimiting the image structure.

In an embodiment, the first soft tissue structure and/or the first bone image structure are compared with the corresponding image structures in the MR image dataset by a geometrical parameter of the respective image structure. The comparison on the basis of a geometrical parameter includes the advantage that comparisons may be made between measurable variables, for example numbers and/or vectors, e.g. for automatic or fully automatic comparisons. A geometrical parameter may involve the volume, the surface content, and/or a curvature parameter of a three-dimensional image structure. A geometrical parameter may include the surface content, the length of the limiting contour and/or a curvature parameter of a two-dimensional image structure. A two-dimensional image may be determined from a three-dimensional image by a section or a projection. A geometrical parameter may also include the position of the image structure.

In an embodiment, the comparison of the first soft tissue structure and/or the first bone structure with the corresponding image structures in the MR image dataset may be made by a self-learning system. For a self-learning system the comparison is not based on the possibly subjective impression of a user. By comparison with non-self-learning systems, a self-learning system includes parameters in the comparison that are not seen as relevant by an operator. The self-learning method is based on a database that contains at least MR image datasets, associated first synthetic electron density maps (input dataset) and also associated parameters for the quality (quality parameters, output dataset) of the match between a synthetic electron density map with the associated MR image dataset. A quality parameter may involve a number, but a quality parameter may also involve a binary value. In an embodiment, the determination of a corrected synthetic electron density map is undertaken in a self-learning manner based on a database, that includes at least MR image datasets, associated first synthetic electron density maps, and associated corrected synthetic electron density maps. For, a self-learning system a determination of the corrected synthetic electron density map is not based on the possibly subjective impression of a user. By comparison with non-self-learning systems, a self-learning system includes corrected synthetic electron density map parameters that are not seen as relevant by an operator or a person skilled in the art. The MR image dataset and the first synthetic electron density map may be used as the input dataset and the corrected synthetic electron density map as the output dataset. The training of the self-learning system may be undertaken by datasets in which the operator includes determining an associated corrected synthetic electron density map based on the MR image dataset and the first synthetic electron density map.

In an embodiment, a plan for the radiation therapy-based treatment (radiotherapy plan) of a target volume within the patient is determined using the corrected synthetic electron density map. The radiotherapy plan is determined exclusively on the basis of an MR image dataset of the patient. Other imaging methods such as CT imaging are not employed. The target volume may include a tumor. The radiotherapy plan is, for example, loaded from a database and/or created by a planning program. The radiotherapy plan, for example, includes settings for a radiotherapy device, by which a radiation therapy of the target volume may be performed. In the case of an external radiation therapy of the target volume by a linear accelerator, the radiotherapy plan may for example include radiotherapy angles, settings of collimators, radiotherapy energies, radiotherapy durations etc. The radiotherapy plan may either be matched specifically to the radiotherapy of the patient or may be a standard radiotherapy plan.

In an embodiment, a dose distribution in a planning volume is determined on the basis of the treatment plan and the corrected synthetic electron density distribution. The dose distribution is determined exclusively on the basis of an MR image dataset of the patient. Further imaging methods such as CT imaging are not employed. The planning volume is selected such that the volume includes the target volume or is identical to the volume. The dose distribution may specify a spatially resolved distribution of the dose values, that is present when the patient undergoes radiotherapy on the basis of the radiotherapy plan with a radiotherapy device and when the electron density in the planning volume is embodied in accordance with the corrected synthetic electron density map.

The individual acts of the described method may be performed both automatically and also fully automatically. Automatic, within the context of the present application, implies that the respective act runs autonomously by a computing or image processing unit, and little no interaction between an operator and the imaging system is necessary for the respective act. The computing activity for acts such as an automatic determination, an automatic comparison or an automatic correction is carried out by the computing or image processing unit. The operator may confirm computed results or carry out intermediate acts. In further embodiment with acts carried out fully automatically, no interaction at all by an operator is necessary to carry out the acts. Regardless of whether the individual acts are executed automatically or fully automatically, the method may be an element of a workflow, that requires an interaction with an operator. The interaction with the operator may include of the operator manually selecting a recording protocol and/or a clinical problem, for example from a menu presented by a screen.

Embodiments further relate to an image processing unit, a computer program product, a computer-readable storage medium and also to a magnetic resonance device, that is configured to carry out the described method.

In a magnetic resonance device, also referred to as a magnetic resonance tomography system, the body of a person to be examined, for example, a patient, is subjected with the aid of a main magnet to a relatively high main magnetic field, for example of 1.5 or 3 or 7 Tesla. In addition, gradient pulses are applied with the aid of a gradient pulse unit. Then, via a radio-frequency antenna unit, radio-frequency pulses, for example, excitation pulses, are emitted by suitable antenna devices, that leads to the nuclear spins of specific atoms resonantly excited by the radio-frequency pulses that are flipped by a defined flip angle in relation to the magnetic field lines of the main magnetic field. During the relaxation of the nuclear spin, radio-frequency signals, magnetic resonance signals, are radiated out, that are received by suitable radio-frequency antennas and are then further processed. Finally, the desired image data may be reconstructed from the raw data acquired.

A computation unit is a device that processes data by programmable computation specifications. A computation unit may, for example, include software elements and/or hardware elements, for example a microprocessor or an FPGA (Field Programmable Gate Array). A computation unit may be a computer, a processor, or a microcontroller. A computation unit may, for example, also include interfaces for connections with other computing units, or for connections with input and/or output devices.

An MR image dataset includes, for example, one or more two-dimensional (2D) or three-dimensional (3D) images of a region of a human body, that have been determined by MR imaging. Different parameters may be selected for the data recording and/or the image reconstruction for different images. For example, the parameters may be chosen so that by using Dixon's methods (Dixon: "Simple proton spectroscopic imaging" Radiology 153 (1984), P. 189-194), in-phase images and out-of-phase images are created, that may be used for reconstruction of fat and water images. If such different images are present in an image dataset, further method acts may use individual images of the images for example. Acts may use a subset or all of the images. Acts may use an effective overall image that is based on a subset of the images or on all of the images. Different images of the same image dataset may represent different regions of the human body. The different images of the same image dataset may also be recorded at different points in time.

An electron density map includes, for example, a spatially resolved distribution of an electron density. An electron density map may be a two-dimensional or three-dimensional map. The entries in an electron density map may include units that characterize an electron density for example, such as for example a coefficient of linear attenuation with a unit of 1/m. The first electron density map may represent the spatially resolved distribution of the electron density in the patient, that is exclusively determined on the basis of the MR image dataset. The first electron density map is established, for example, exclusively using the MR image dataset of the patient to be treated. For example, no further medical imaging data of the patient to be treated except for the MR image dataset is included for establishing the first electron density map. However, further image datasets, for example CT image datasets, from other patients may be included. The first electron density map may include medical image data in the same patient geometry of the MR image dataset, however with a gray value distribution that would be present, had CT image data of the same patient been acquired. The first electron density map may be used for the MRORTP.

Methods for establishing the first electron density map from the magnetic resonance image data are based, for example, on a fully automatic, automatic, or manual segmentation of the magnetic resonance image data into different tissue classes, such as for example water, fat, air, possibly bones. The first electron density map may be determined from the magnetic resonance image dataset by a magnetic resonance-tomography computed tomography atlas (MR-CT atlas). The magnetic resonance image data may be acquired by a specific magnetic resonance sequence, that may employ ultrashort echo times, so that magnetic resonance signals may be received from bones of the patient. A masking of the magnetic resonance image data for establishing bone and/or air masks for the computation of the first electron density map is possible. A multi-contrast magnetic resonance imaging may provide a basis for the segmentation of the magnetic resonance image data for creation of the first electron density map. Further possible methods for establishing the first electron density map from the magnetic resonance image data may be based on pattern recognition and/or image normalization and/or classification and/or bias field estimation.

An MR-CT atlas may include a database, in which the MR image datasets of a first patient volume, CT image datasets of a second patient volume and the associated registrations are stored where the first and the second patient volumes at least overlap. As an alternative, the transformed image datasets based on a registration may also be stored. The collection of the MR and CT image datasets may be generated by combined MR/CT devices, where no registration is necessary, or by two different devices, in that a number of image datasets are recorded from the same patient at different points in time. In the case of different devices, a non-trivial registration transformation is determined, that compensates for the differences that arise for the choice of the different points in time and the different support in the two devices. The determination of a synthetic electron density by an MR-CT atlas is known (cf. Jason A. Dowling et al.: "Automatic Substitute Computed Tomography Generation and Contouring for Magnetic Resonance Imaging (MRI)-Alone External Beam Radiation Therapy From Standard MRI Sequences", in: Int. J. Radiat. Oncol. Biol. Phys. 93 (2015), Pages 1144-1153). Other methods for establishing the synthetic CT image data, e.g. of the first electron density map, from the magnetic resonance image data may be known and used.

Methods for establishing the first electron density map from the magnetic resonance image data, however exhibit a different precision and/or robustness, for example, concerning the bone regions in the patient. With many algorithms, the result may be incorrect assignments of bones, soft tissue, or air in specific regions. Also trapped air in the patient (air regions or air pockets) may lead to problems in the correct assignment of the electron density to the magnetic resonance image data. An estimate for an MRORTP may be used as to whether a reliable dose calculation may be carried out on the basis of the calculated first synthetic electron density map, i.e. the synthetic CT image data, or whether a corrected synthetic electron density map is determined.

Registration of two image datasets refers to matching two different image datasets of the same or similar patient volumes to one another. For example, a transformation function may be applied to one of the two image datasets. In medical imaging, the similar original images may, for example, involve the same patient at different points in time. The differences in the original image may be produced by a change of the location of the patient or by a change in the anatomical circumstances between the two points in time, such as e.g. by the progress of metabolism processes or by a different degree of filling of the lungs.

A body region is a functionally contiguous subunit of a patient, or a part of a functionally contiguous subunit of a patient. Soft tissue regions are all body regions of a patient that are not bones, for example, organs as well as muscle, nerve or supporting tissue, or the parts. The skin of a patient may also be described as a soft tissue region. Bone regions are all body regions of a patient, that are bony, for example, bones and parts of bones.

An image structure is the mapping of a body region in an image dataset. A soft tissue image structure is the mapping of a soft tissue region in an image dataset. A bone image structure is the mapping of a bone region in an image dataset. An image structure corresponds to a body region if the image structure is the mapping of the body region in an image dataset. An image structure may be defined as a set of pixels or voxels that belong together in an image dataset. For example, deviations between the form and the position of image structures and body regions corresponding to one another may be produced by errors in the imaging and/or in the image reconstruction.

An image structure in a first image dataset corresponds to an image structure in a second image dataset, when the two image structures correspond to the same body region of the same patient. Errors in the two imaging methods and/or the two image reconstructions of the two image datasets may cause deviations to arise between the shape and the position of the image structures corresponding to one another. If the two image datasets map the same part of the patient and have the same parameters, such as e.g. orientation and resolution, deviations arise, for example, in such a way that pixels or voxels are assigned to the image structure in the first image dataset, but not to the image structure in the second image dataset.

At least one first soft tissue image structure and/or at least one first bone image structure in the first synthetic electron density map may be defined, for example, by a segmentation. A segmentation refers to the creation of structures that belong together in an image dataset by grouping together adjacent pixels or voxels that have a common characteristic. Pixels or voxels that are parts of the image of the same body region are assigned to a common region. The segmentation may, for example, involve a threshold value segmentation, in which pixels or voxels are classified as belonging to a soft tissue image structure if a value lies below a threshold value, and are classified as belonging to a bone image structure if a value lies above the threshold value, or vice versa. A number of threshold values may also be used to define a number of soft tissue image structures and/or a number of bone image structures. The value of a pixel or voxel may be specified in Hounsfield units for example. The determination of at least one soft tissue image structure and/or of at least one bone image structure may also be done by self-learning method. The self-learning method may be trained, for example, with a plurality of first synthetic electron density maps created from MR image datasets, in which first soft tissue and first bone image structures have already been determined.

A self-learning system establishes a transformation function that maps an input dataset onto an output dataset. The transformation function is established by training. A self-learning system may be based, for example, on an artificial neural network that maps an input dataset onto an output dataset by linear or non-linear transformations and weights to be determined. The weights of the artificial neural network may, for example, be determined by training, for example by using a back propagation algorithm on the basis of existing assignments of input datasets to output datasets. The weights of the artificial neural network may be determined based on input and output datasets of a specific device and/or of a specific operator, but the weights may also be determined from a database, in which input and output datasets of different devices and/or different users are stored. The training may also already be undertaken before the claimed method is used, i.e. an artificial neural network with defined weights may already be used in the method.

A comparison of the first soft tissue image structure and/or of the first bone image structure with the corresponding image structures in the MR image dataset is made by a second soft tissue image structure and/or a second bone image structure are determined in the MR image dataset. The first soft tissue image structure from the first synthetic electron density map is compared with the second soft tissue image structure from the MR image dataset, and/or the first bone image structure from the first synthetic electron density map is compared with the second bone image structure from the MR image dataset. The comparison may be made for example pixel-by-pixel or voxel-by-voxel. The comparison may also be made, for example, by a geometrical parameter. A geometrical parameter may relate to the volume of the image structures in the respective image dataset, the surface content of the surface image structures in the respective image dataset, or a measure of curvature of the image structures in the respective image dataset. The comparison may be based on two-dimensional sections through a three-dimensional image structure in the image dataset, or on two-dimensional projections of a three-dimensional image structure, as well as, for example, to geometrical dimensions of the sections or projections such as surface content and extent. The geometrical parameter may also include the position of the soft tissue image structure and/or of the first bone image structure in the first synthetic electron density map with the corresponding image structures in the MR image dataset. A comparison of any type may also contain the assessment on the basis of a quality parameter. The comparison may also be made by an operator. The combination is output by an output device such as a screen or a printer, to the user, and an input quality parameter may be received. The comparison may also be made automatically or fully automatically. The comparison may, for example, also be based on different image data of the MR image dataset, that correspond to different recording parameters or image reconstruction parameters. For example, an out-of-phase image in accordance with the method of Dixon organ boundaries shows up dark. The image may be used to compare mappings of organs in the MR image dataset with the corresponding soft tissue image structure of the first synthetic electron density map.

The determination of a corrected synthetic electron density map, that is better matched to the actual electron density of the patient, may be undertaken with the corrected synthetic electron density map identical to the first synthetic electron density map. A corrected synthetic electron density map may however also be determined based on the comparison of the first synthetic electron density map with the MR image dataset, by at least one soft tissue image structure and/or at least one bone image structure changed, and the pixel values or voxel values of the corrected synthetic electron density map determined based on the pixel values or voxel values of the first synthetic electron density map and/or on the assignment of a pixel or voxel to an original and/or changed image structure. The value of a pixel or voxel in the corrected synthetic electron density map may be able to be determined based on the value of the corresponding pixel or voxel in the first synthetic electron density map and as the pixel or voxel is a part of a bone image structure or soft tissue image structure. The average electron density of a soft tissue region or of a bone region may be selected for the value of a pixel or voxel, depending on whether the pixel or voxel belongs to a soft tissue image structure or a bone image structure. The average electron density of a soft tissue region may be determined as the average value of the electron density of the pixels or voxels that belong to a soft tissue image structure. The average electron density of a bone region as the average value of the electron density of the pixels or voxels that belong to a bone image structure. A soft tissue image structure and/or a bone image structure may be changed such that pixels or voxels are assigned to a soft tissue image structure or a bone image structure, or that pixels or voxels are removed from a soft tissue image structure or a bone image structure. A soft tissue image structure and/or a bone image structure may be changed such that a number of soft tissue image structures and/or bone image structures, that are mappings of a single soft tissue region and/or bone region of the body, but are incorrectly classified as different image structures, are grouped together.

DETAILED DESCRIPTION

Figure 1:
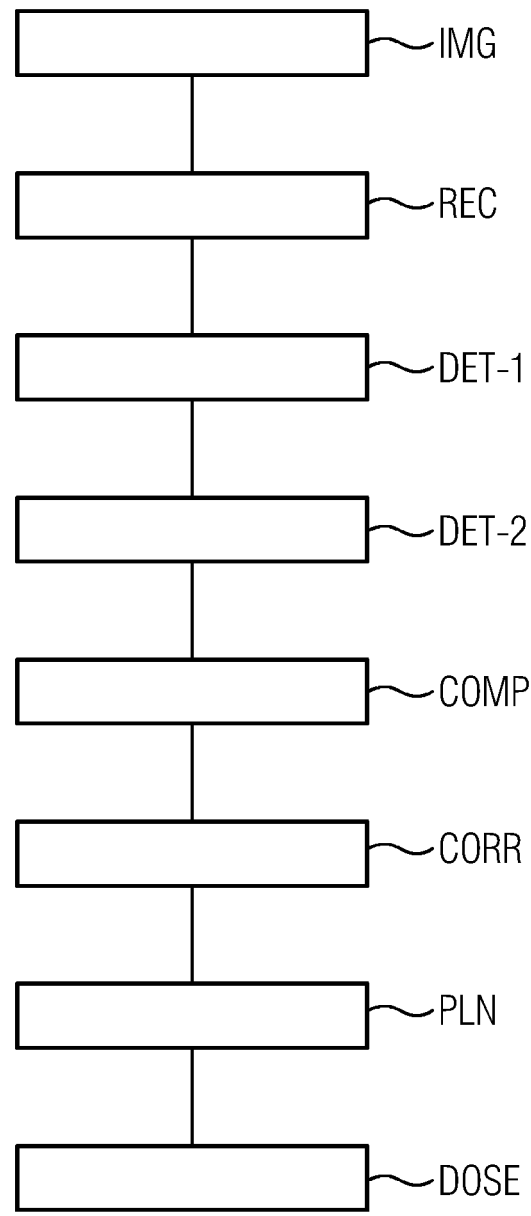
FIG. 1 depicts a flow diagram of a method for determining a corrected synthetic electron density map according to an embodiment.

FIG. 1 depicts a flow diagram of a method for determining a corrected synthetic electron density map 54. The first act is the recording of an image IMG of an MR image dataset 41 by an MR device 30. The MR image dataset 41 is received REC by an image processing unit 20 by an interface 21. On the basis of the MR image dataset 41 and an MR-CT atlas, a synthetic electron density map 40 is determined DET-1. Datasets are determined from the MR-CT atlas on the basis of parameters of the patient 33 (including for example age, gender, weight, special anatomical features), that have similarities to the actual anatomy of the patient 33. From the datasets, an effective or average bone image structure 45 is determined that is inserted into the synthetic electron density map 40. All pixels or voxels of the electron density map 40 that are not part of the bone image structure are allocated the average electron density of soft tissue. As an alternative, the soft tissue region of the body that the pixel or voxel is mapping may also be established, and the pixel or voxel may be allocated the average electron density of the soft tissue region. At the determination DET-2 of a soft tissue image structure 43, all soft tissue regions are mapped in the image dataset, and of a bone image structure 45, that includes all bone regions mapped in the image dataset. The determination DET-2 may be undertaken by a threshold value segmentation. An electron density that lies between the average electron density of soft tissue regions and the average electron density of bone regions is used as the threshold value. The comparison COMP of the soft tissue image structure 43 is determined and the bone image structure 45 is determined with the MR image dataset 41, in that the contour 51 of the soft tissue image structure 43 and the contour 48 of the bone image structure 45 are displayed directly in the MR image dataset 41. In an embodiment, the contour 51 of the soft tissue image region 41 corresponds to the contour of the patient 33. CORR determines a corrected synthetic electron density map 54, by an artificial neural network, receives input data the MR image dataset 41 as well as determines the contours 48, 51 of the image structures 43, 45, and creates a corrected synthetic electron density map 54. The network is trained by a plurality of datasets (including MR image datasets 41, contours 48, 51 of image structures 43, 45 from the electron density map 40 and corrected electron density maps 54). In the training phase, the corrected electron density maps 54 are created by a user such that the geometry of the image structures 43, 45 are corrected based on the MR image dataset 41. Pixels or voxels, that belonged after correction to another image structure, have been allocated average electron densities of the respective corresponding body region. Based on the corrected synthetic electron density map 54, a radiotherapy is planned (PLN), such that a target region of the body is subjected to a radiation dose determined by the operator. Based on the radiotherapy planning and the corrected synthetic electron density map 54, the dose distribution DOSE may be determined in the part of the patient that is mapped in the MR image dataset 41. The target body region, as well as the organs at risk, are localized by the MR image dataset 51.

Figure 2:
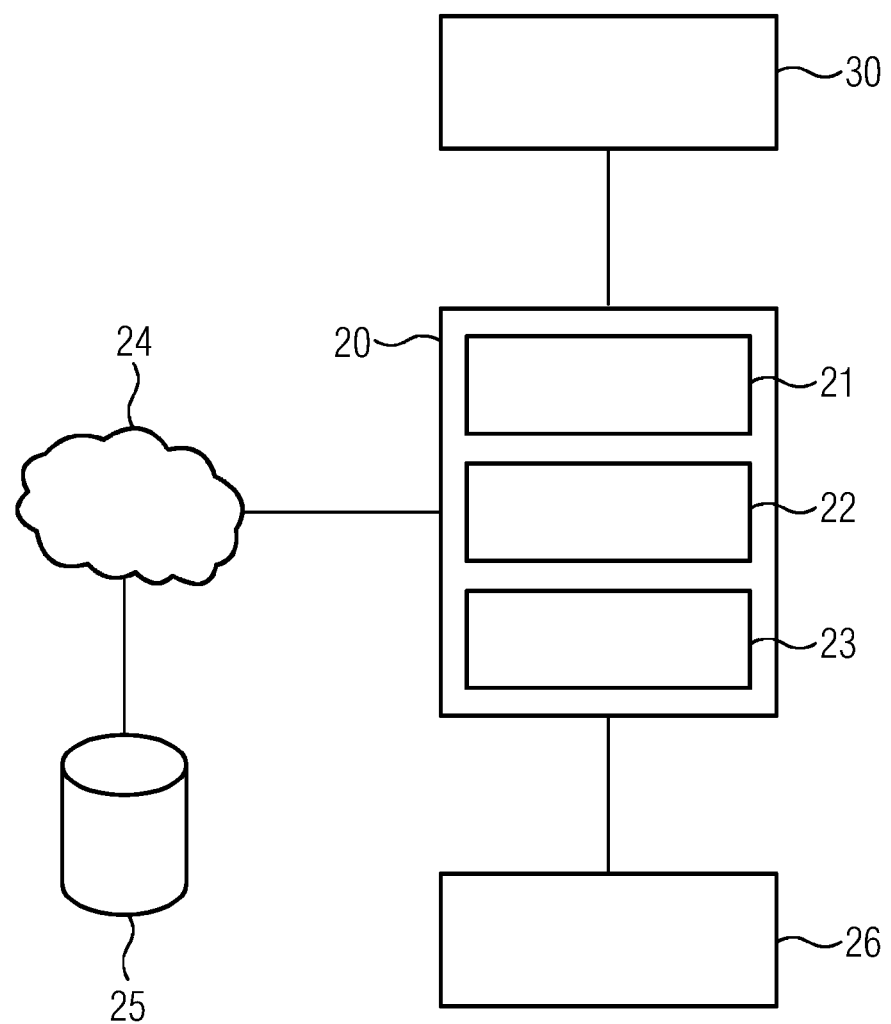
FIG. 2 depicts an image processing unit according to an embodiment.

FIG. 2 depicts an image processing unit. The image processing unit 20 is programmed to carry out the method for determining a corrected synthetic electron density 54. The image processing unit 20 includes an interface 21, a computation unit 22 and also an input and output unit 23. The image processing unit 20 is connected to an MR imaging device 30 and to a radiotherapy device 26. The interface 21 involves hardware or software interfaces, for example the hardware interfaces PCI bus, USB or Firewire. The computation unit 22 may have software elements and hardware elements, for example a microprocessor or an FPGA (Field Programmable Gate Array). The computation unit 22 may be a part of a computer. The image processing unit 20 may communicate with a database 25. In the embodiment depicted, the image processing unit 20 is connected via a network 24 to the database. The network may be the Internet or by an intranet for example, or by an interface connection. The image processing unit 20 may have further interfaces.

Figure 3:
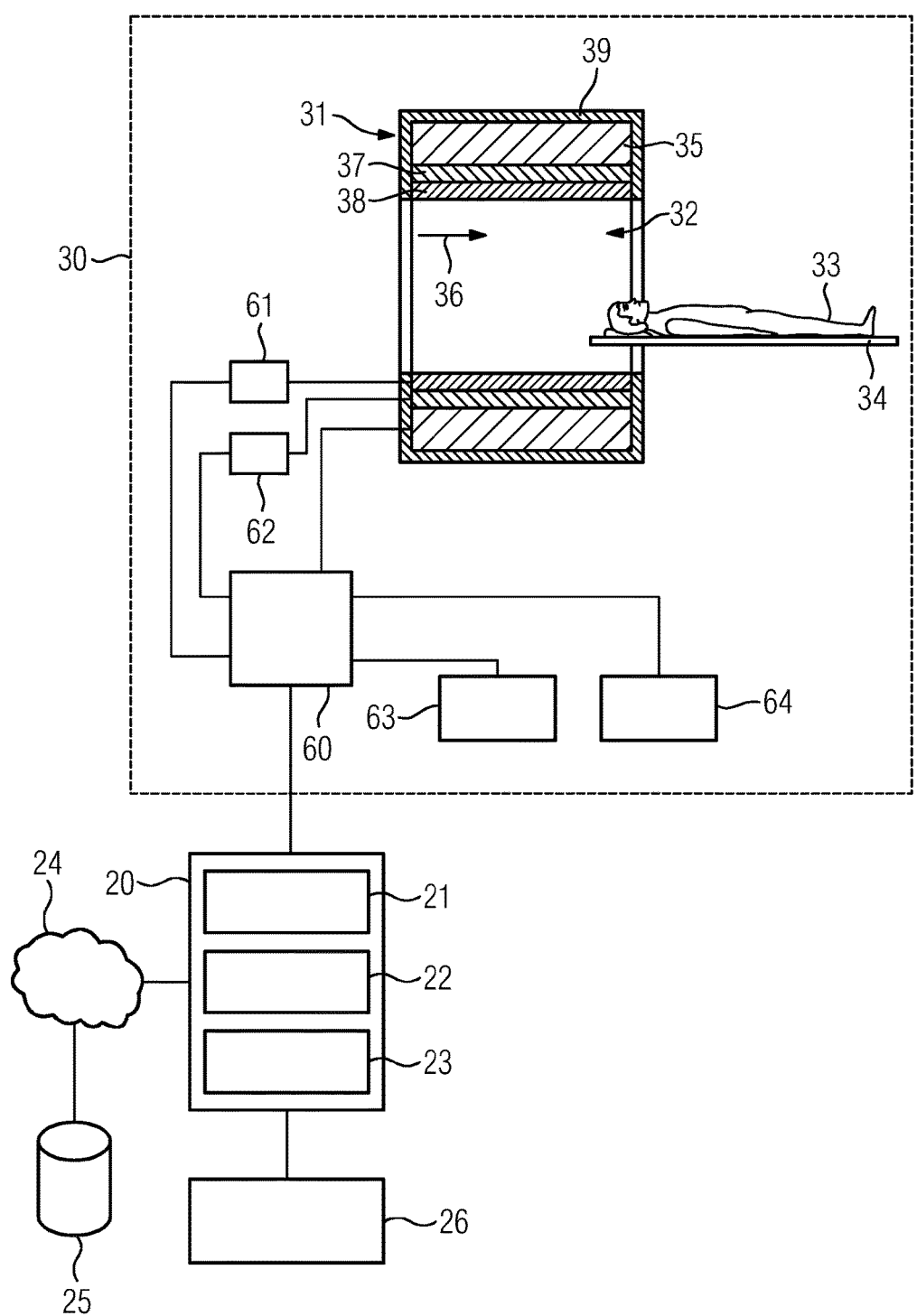
FIG. 3 depicts a magnetic resonance imaging device according to an embodiment.

FIG. 3 depicts a schematic diagram of a magnetic resonance device 30. The magnetic resonance device 30 includes a detector unit formed by a magnet unit 31 with a main magnet 35 for creating a strong and, for example, constant main magnetic field 36. In addition, the magnetic resonance device 30 includes a cylindrical patient receiving area 32 for receiving a patient 33. The patient receiving area 32 is surrounded in a circumferential direction by the magnet unit 31 in the shape of a cylinder. The patient 33 may be pushed by a patient support facility 34 of the magnetic resonance device 30 into the patient receiving area 32. The patient support facility 34 includes a patient table that is arranged so as to be able to be moved within the magnetic resonance device 30. The magnet unit 31 is screened from the outside by a housing cladding 39 of the magnetic resonance device.

The magnet unit 31 also includes a gradient coil unit 37 for generating magnetic field gradients, that are used for a spatial encoding during imaging. The gradient coil unit 37 is controlled by a gradient control unit 62. The magnet unit 31 includes a radio-frequency antenna unit 38, that in the case shown, is a body coil permanently integrated into the magnetic resonance device 30, and a radio-frequency antenna control unit 61 for exciting a polarization, that occurs in the main magnetic field 36 generated by the main magnet 35. The radio-frequency antenna unit 38 is controlled by the radio-frequency antenna control unit 61 and radiates radio-frequency magnetic resonance sequences into an examination room, that is formed by the patient receiving area 32. The radio-frequency antenna unit 38 is configured for receiving magnetic resonance signals, for example, from the patient 33.

To control the main magnet 35, the gradient control unit 62 and the radio-frequency antenna control unit 61, the magnetic resonance device 30 includes an MR computation unit 60. The MR computation unit 60 centrally controls the magnetic resonance device 30, such as, for example, carrying out of a predetermined imaging gradient echo sequence. Control information, such as for example imaging parameters, as well as reconstructed magnetic resonance images, may be provided at a provision unit 63, in the present case a display unit 63, of the magnetic resonance device 30 for a user. In addition, the magnetic resonance device 30 includes an input unit 64, by which information and/or parameters may be entered during a measurement process by a user. The MR computation unit 60 may include the gradient control unit 62 and/or radio-frequency antenna control unit 61 and/or the MR display unit 63 and/or the MR input unit 64.

The magnetic resonance device 30 depicted may also include further components that magnetic resonance devices 30 have. The manner in which a magnetic resonance device 30 functions is also known.

Connected to the magnetic resonance device depicted is an image processing unit 20, including an interface 21, a computation unit 22 and an input and/or output unit 23. The image processing unit 20 is connected to a radiotherapy unit 26 and a database 25. The image processing unit 20 is configured for carrying out the method.

In other embodiments, the MR computation unit 60 may also be identical to the computation unit 22 of the image processing unit 20. The image processing unit 20 is a control and image processing unit. The MR display unit 63 and the input and output unit 23 may be identical. The MR input unit 64 and the input and output unit 23 may be identical.

Figure 4:
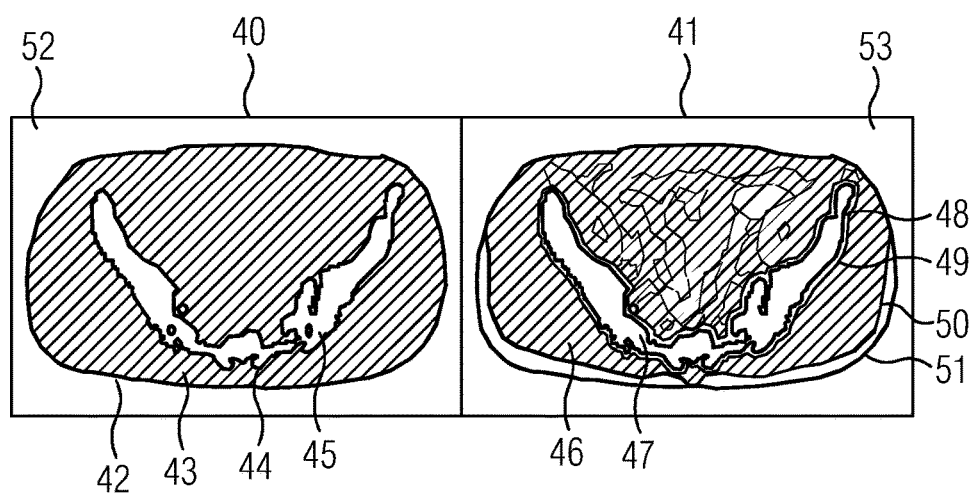
FIG. 4 depicts an example result image including a synthetic electron density map and an MR image dataset.

FIG. 4 depicts a result image including a first synthetic electron density map 40 and an MR image dataset 41 that both map the same part of a patient 33. The first synthetic electron density map 40 is created from the MR image dataset 41.

The first synthetic electron density map further includes at least one first soft tissue image structure 43, one first bone image structure 45, and a patient environment 52 that may correspond to the ambient air. The first synthetic electron density map depicted includes the edge 42 of the first soft tissue image structure 43 and the edge 44 of the first bone image structure 45.

The MR image dataset 41 includes at least one second soft tissue image structure 46 and the edge 50 of the second soft tissue image structure. The MR image dataset includes a second bone image structure 47 and the edge 48 of the second bone image structure. The MR image dataset includes the representation of the patient environment 53, that corresponds to the ambient air. The second soft tissue image structure 46 and the first soft tissue image structure 43 correspond to the same soft tissue region in the patient 33. The second bone image structure 47 and the first bone image structure 46 correspond to the same bone region in the patient 33.

The representation of the MR image dataset mapped includes the edge 51 of the first soft tissue image structure, that precisely corresponds to the edge 42 of the first soft tissue image structure in the first synthetic electron density map. The representation of the MR image dataset mapped includes the edge 49 of the first bone image structure, that precisely corresponds to the edge 44 of the first bone image structure in of the first synthetic electron density map. The edge 49 of the first bone image structure differs from the edge 48 of the second bone image structure, and the edge 51 of the first soft tissue image structure differs from the edge 50 of the second soft tissue image structure. The difference may be produced by errors in the determination of the electron density map or the difference may be produced by errors in the determination of the first soft tissue image structure 43 and the first bone image structure 45 in the electron density map.

Figure 5:
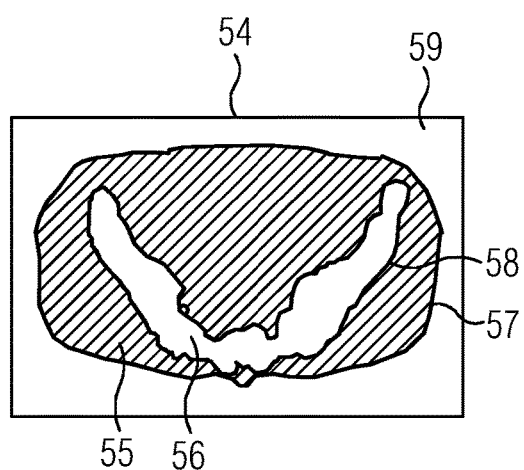
FIG. 5 depicts an example corrected synthetic electron density map.

FIG. 5 depicts the corrected synthetic electron density map 54 that was determined by the result image (including the first synthetic electron density map 40 and the MR image dataset 41). The first synthetic electron density map 40 is changed such that the shape and size of the soft tissue image structure 55 of the corrected synthetic electron density map correspond to that of the soft tissue image structure 46 of the MR image dataset 41, and that the shape and size of the bone image structure 47 of the corrected synthetic electron density map correspond to that of the bone image structure 46 of the MR image dataset 41. Also depicted in the corrected synthetic electron density map are the edge 57 of the soft tissue image structure 55 and the edge 58 of the bone image structure 56, as well as the environment 59 of the patient 33, that is formed by air.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining a corrected synthetic electron density map, the method comprising:
   acquiring, using a magnetic resonance (MR) device, at least one magnetic resonance image dataset taken of a patient;
   determining, by a processor, a first synthetic electron density map of the patient based on the at least one magnetic resonance image dataset taken of the patient;
   determining, by the processor, at least one first soft tissue image structure of the patient, at least one first bone image structure of the patient, or at least one first soft tissue image structure and at least one first bone image structure of the patient based on the first synthetic electron density map;
   comparing, by the processor, the first soft tissue image structure, the first bone image structure, or the first soft tissue image structure and the first bone image structure from the first synthetic electron density map with corresponding image structures in the [ [MR]] at least one magnetic resonance image dataset taken of the patient;
   determining, by the processor, a corrected synthetic electron density map, the determining of the corrected synthetic electron density map comprising correcting the first soft tissue image structure, the first bone image structure, or the first soft tissue image structure and the first bone image structure, based on the comparison; and
   creating, by the processor, a plan for a radiation based treatment of a target volume of the patient based on the corrected synthetic electron density map.

2. The method of claim 1, wherein the comparison is made such that the first soft tissue image structure, the first bone image structure, or the first soft tissue image structure and the first bone image structure are combined with the at least one magnetic resonance image dataset taken of the patient in a result image.

3. The method of claim 2, wherein the result image comprises the at least one magnetic resonance image dataset taken of the patient, wherein at least a part of the first soft tissue image structure, at least a part of the first bone image structure, or at least a part of the first soft tissue image structure and at least a part of the first bone image structure is shown in the at least one magnetic resonance image dataset taken of the patient.

4. The method of claim 3, wherein the part of the first soft tissue image structure, the part of the first bone image structure, or the part of the first soft tissue image structure and the part of the first bone image structure comprise at least an edge of the first soft tissue image structure, an edge of the first bone image structure, or the edge of the first soft tissue image structure and the edge of the first bone image structure.

5. The method of claim 1, wherein the comparison is made based on a geometrical parameter of the soft tissue image structure, a geometrical parameter of the bone image structure, or the geometrical parameter of the soft tissue image structure and the geometrical parameter of the bone image structure as well as a geometrical parameter of the corresponding image structures in the at least one magnetic resonance image dataset taken of the patient.

6. The method of claim 1, wherein the comparison is made in a self learning manner by a database, wherein the database contains at least MR image datasets, associated first synthetic electron density maps, and associated parameters for the quality of the match between an MR image dataset and a synthetic electron density map.

7. The method of claim 1, wherein the determining of the corrected synthetic electron density map comprises determining in a self learning manner by a database, wherein the database contains at least MR image datasets, associated first synthetic electron density maps, and associated corrected synthetic electron density maps.

8. The method of claim 1, further comprising:
   computing a dose distribution in at least one planning volume of the patient based on the corrected synthetic electron density map and the plan for a radiation based treatment.

9. An image processing unit, the image processing unit comprising:
   a computer configured to determine a corrected synthetic electron density map, the determination of the corrected synthetic electron density map comprising:
      acquiring at least one magnetic resonance image dataset taken of a patient from an magnetic resonance device;
      determination of a first synthetic electron density map of the patient based on the at least one MR image dataset;
      determination of at least one first soft tissue image structure of the patient, at least one first bone image structure of the patient, or at least one first soft tissue image and at least one first bone image structure of the patient based on the first synthetic electron density map;
      comparison of the first soft tissue image structure, the first bone image structure, or the first soft tissue image structure and the first bone image structure from the first synthetic electron density map with corresponding image structures in the at least one magnetic resonance image dataset taken of the patient;
      determination of a corrected synthetic electron density map, the determination of the corrected synthetic electron density map comprising correction of the first soft tissue image structure, the first bone image structure, or the first soft tissue image structure and the first bone image structure, based on the comparison;

a display configured to display the corrected synthetic electron density map; and a processor configured to create a plan for a radiation based treatment of a target volume of the patient based on the corrected synthetic electron density map.

10. The image processing unit of claim 9, wherein the comparison is made such that the first soft tissue image structure, the first bone image structure, or the first soft tissue image structure and the first bone image structure are combined with the at least one magnetic resonance image dataset taken of the patient in a result image.

11. The image processing unit of claim 9, wherein the result image comprises the at least one magnetic resonance image dataset taken of the patient, wherein at least a part of the first soft tissue image structure, at least a part of the first bone image structure, or at least a part of the first soft tissue image structure and at least a part of the first bone image structure are shown in the at least one magnetic resonance image dataset taken of the patient.

12. The image processing unit of claim 11, wherein the part of the first soft tissue image structure, the part of the first bone image structure, or the part of the first soft tissue image structure and the part of the first bone image structure comprise at least an edge of the first soft tissue image structure, an edge of the first bone image structure, or the edge of the first soft tissue image structure and the edge of the first bone image structure.

13. The image processing unit of claim 9, wherein the comparison is made based on a geometrical parameter of the soft tissue image structure, a geometrical parameter of the bone image structure, or the geometrical parameter of the soft tissue image structure and the geometrical parameter of the bone image structure as well as a geometrical parameter of the corresponding image structures in the at least one magnetic resonance image dataset taken of the patient.

14. The image processing unit of claim 9, wherein the comparison is made in a self learning manner by a database, wherein the database contains at least MR image datasets, associated first synthetic electron density maps, and associated parameters for the quality of the match between an MR image dataset and a synthetic electron density map.

15. A computer program product comprising a non-transitory computer-readable storage medium storing instructions executable by one or more processors to determine a corrected synthetic electron density map, the instructions comprising:
  determining a first synthetic electron density map of a patient based on at least one magnetic resonance image dataset taken of the patient;
  determining at least one first soft tissue image structure of the patient, at least one first bone image structure of the patient, or at least one first soft tissue image and at least one first bone image structure of the patient based on the first synthetic electron density map;
  comparing the first soft tissue image structure, the first bone image structure, or the first soft tissue image structure and the first bone image structure from the first synthetic electron density map with corresponding image structures in the at least one magnetic resonance image dataset taken of the patient;
  determining a corrected synthetic electron density map, the determining of the corrected synthetic electron density map comprising correcting the first soft tissue image structure, the first bone image structure, or the first soft tissue image structure and the first bone image structure, based on the comparison; and
  determining a plan for a radiation based treatment of a target volume of the patient based on the corrected synthetic electron density map.

16. A non-transitory computer readable medium storing computer program instructions for determining a corrected synthetic electron density map, the computer program instructions, when executed by a processor, causing the processor to perform operations comprising:
  determining a first synthetic electron density map of a patient based on at least one magnetic resonance image dataset taken of the patient;
  determining at least one first soft tissue image structure of the patient, at least one first bone image structure of the patient, or at least one first soft tissue image and at least one first bone image structure of the patient based on the first synthetic electron density map;
  comparing the first soft tissue image structure, the first bone image structure, or the first soft tissue image structure and the first bone image structure from the first synthetic electron density map with corresponding image structures in the at least one magnetic resonance image dataset taken of the patient;
  determining a corrected synthetic electron density map, the determining of the corrected synthetic electron density map comprising correcting the first soft tissue image structure, the first bone image structure, or the first soft tissue image structure and the first bone image structure, based on the comparison; and
  determining a plan for a radiation based treatment of a target volume of the patient based on the corrected synthetic electron density map.

17. A system comprising:
a magnetic resonance device, the magnetic resonance device configured to record at least one magnetic resonance image dataset taken of a patient;
an image processing unit comprising:
  a computation unit configured to determine a corrected synthetic electron density map, the determination of the corrected synthetic electron density map comprising:
    determination of a first synthetic electron density map of the patient based on the at least one magnetic resonance image dataset taken of the patient;
    determination of at least one first soft tissue image structure of the patient, at least one first bone image structure of the patient, or at least one first soft tissue image and at least one first bone image structure of the patient based on the first synthetic electron density map;
    comparison of the first soft tissue image structure, the first bone image structure, or the first soft tissue image structure and the first bone image structure from the first synthetic electron density map with corresponding image structures in the at least one magnetic resonance image dataset taken of the patient;
    determination of a corrected synthetic electron density map, the determination of the corrected synthetic electron density map comprising correction of the first soft tissue image structure, the first bone image structure, or the first soft tissue image structure and the first bone image structure, based on the comparison;
    creation of a plan for a radiation based treatment of a target volume of the patient based on the corrected synthetic electron density map; and a display configured to display the corrected synthetic electron density map.

* * * * *

UNITED STATES PATENT AND TRADEMARK OFFICE
CERTIFICATE OF CORRECTION

PATENT NO. : 10,363,009 B2
APPLICATION NO. : 15/713068
DATED : July 30, 2019
INVENTOR(S) : Martin Requardt et al.

Page 1 of 1

It is certified that error appears in the above-identified patent and that said Letters Patent is hereby corrected as shown below:

On the Title Page

(74) Attorney, Agent, or Firm:
"Sempia Summerfield Katz, LLC"
Should be replaced with:
"Lempia Summerfield Katz, LLC"

Signed and Sealed this
Eighth Day of October, 2019

Andrei Iancu
*Director of the United States Patent and Trademark Office*